(12) United States Patent
Moore et al.

(10) Patent No.: US 9,878,100 B2
(45) Date of Patent: *Jan. 30, 2018

(54) MEDICATED MODULE WITH AUTOMATIC RESERVOIR ENGAGEMENT

(75) Inventors: David Moore, Leicester (GB); Garen Kouyoumjian, Leamington Spa (GB); Christopher John Jones, Tewkesbury (GB); James Mark Watson, Edinburgh (GB); John David Cross, Northhampton (GB); Malcolm Stanley Boyd, Wellsbourne (GB); Alasdair George Young, San Francisco, CA (US); Naceur Rekaya, Leamington Spa (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 1451 days.

This patent is subject to a terminal disclaimer.

(21) Appl. No.: 13/636,569

(22) PCT Filed: Mar. 23, 2011

(86) PCT No.: PCT/EP2011/054426
§ 371 (c)(1),
(2), (4) Date: Mar. 27, 2013

(87) PCT Pub. No.: WO2011/117287
PCT Pub. Date: Sep. 29, 2011

(65) Prior Publication Data
US 2013/0204186 A1    Aug. 8, 2013

Related U.S. Application Data

(60) Provisional application No. 61/317,548, filed on Mar. 25, 2010, provisional application No. 61/331,911, filed on May 6, 2010.

(30) Foreign Application Priority Data

Jul. 21, 2010  (EP) .................................... 10170281
Jul. 21, 2010  (EP) .................................... 10170284

(51) Int. Cl.
*A61M 5/24* (2006.01)
*A61M 5/32* (2006.01)
(Continued)

(52) U.S. Cl.
CPC ........ *A61M 5/2448* (2013.01); *A61M 5/3204* (2013.01); *A61M 5/326* (2013.01);
(Continued)

(58) Field of Classification Search
CPC .............. A61M 5/3204; A61M 5/3257; A61M 5/3271; A61M 5/3272; A61M 5/3297;
(Continued)

(56) References Cited

U.S. PATENT DOCUMENTS 5,429,612 A  7/1995  Berthier
5,779,683 A  7/1998  Meyer
(Continued)

FOREIGN PATENT DOCUMENTS

GB       2445228 A      7/2008
JP     H08509153 A    10/1996
(Continued)

OTHER PUBLICATIONS

English Translation of the Notice of Reasons for Rejection for Japanese Patent Application No. 2013-500490 dated Jan. 6, 2015.
(Continued)

*Primary Examiner* — Bradley Osinski
(74) *Attorney, Agent, or Firm* — McDonnell Boehnen Hulbert & Berghoff LLP

(57) ABSTRACT

A medicated module (4) for an injection system to co-deliver at least two medicaments is disclosed where a primary
(Continued)

delivery device containing a primary medicament accepts a medicated module (4) containing a single dose of a secondary medicament and where both medicaments are delivered through a hollow needle (3). The medicated module (4) does not require the user to manually engage a reservoir (22) containing the secondary medicament. Instead, a biasing member (48) automatically activates the reservoir (22) when the needle guard (42) is retracted. The needle guard (42) prevents accidental needle sticks before and after an injection, and locks after dose delivery.

20 Claims, 6 Drawing Sheets

(51) Int. Cl.
*A61M 5/50* (2006.01)
*A61M 5/315* (2006.01)
*A61M 5/34* (2006.01)
*A61M 5/178* (2006.01)

(52) U.S. Cl.
CPC ......... *A61M 5/5086* (2013.01); *A61M 5/2466* (2013.01); *A61M 5/31525* (2013.01); *A61M 5/31533* (2013.01); *A61M 5/3272* (2013.01); *A61M 5/3294* (2013.01); *A61M 5/3297* (2013.01); *A61M 5/347* (2013.01); *A61M 2005/1787* (2013.01); *A61M 2005/3247* (2013.01); *A61M 2005/3267* (2013.01); *A61M 2205/583* (2013.01)

(58) Field of Classification Search
CPC .... A61M 5/347; A61M 5/2448; A61M 5/284; A61M 5/3294; A61M 2005/3247; A61M 2005/325; A61M 2005/3267; A61M 5/14244; A61M 5/142; A61M 5/145; A61M 5/1452; A61M 2205/58; A61M 2205/502

USPC .................................................. 604/192, 198
See application file for complete search history.

(56) References Cited

U.S. PATENT DOCUMENTS

| | | | |
|---|---|---|---|
| 6,045,534 A | 4/2000 | Jacobsen et al. | |
| 6,547,764 B2* | 4/2003 | Larsen | A61M 5/326 604/110 |
| 6,562,002 B1 | 5/2003 | Taylor | |
| 7,533,293 B2* | 5/2009 | Barlow | G06F 11/0775 714/6.13 |
| 2001/0049496 A1 | 12/2001 | Kirchhofer et al. | |
| 2002/0004648 A1 | 1/2002 | Larsen et al. | |
| 2006/0276755 A1 | 12/2006 | Sullivan et al. | |
| 2009/0018506 A1 | 1/2009 | Daily et al. | |
| 2009/0024093 A1 | 1/2009 | Carrel et al. | |
| 2010/0298768 A1* | 11/2010 | Halili, Jr. | A61J 1/2096 604/87 |
| 2012/0116349 A1* | 5/2012 | Heald | A61M 5/2448 604/506 |

FOREIGN PATENT DOCUMENTS

| | | |
|---|---|---|
| JP | 2003534105 A | 11/2003 |
| WO | 01/76665 A1 | 10/2001 |
| WO | 0191837 A1 | 12/2001 |
| WO | 2010/019936 A1 | 2/2010 |

OTHER PUBLICATIONS

Office Action and Search Report issued in Chinese Patent Application No. 201180025849.2 dated Sep. 10, 2014.
International Preliminary Report on Patentability for Int. App. No. PCT/EP2011/054426, dated Oct. 4, 2012.
International Search Report and Written Opinion for Int. App. No. PCT/EP2011/054426, dated Jun. 21, 2011.
English Translation of the Third Office Action issued in Chinese Patent Application No. 201180025859.2 dated Mar. 23, 2015.

\* cited by examiner

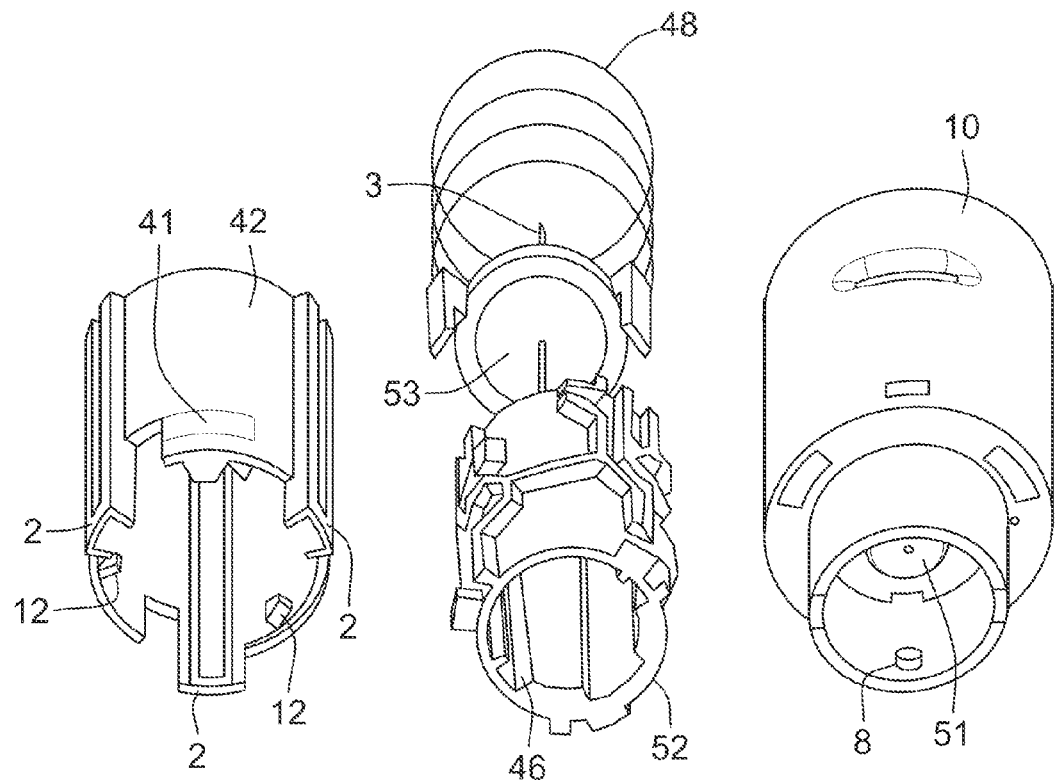
FIG. 4
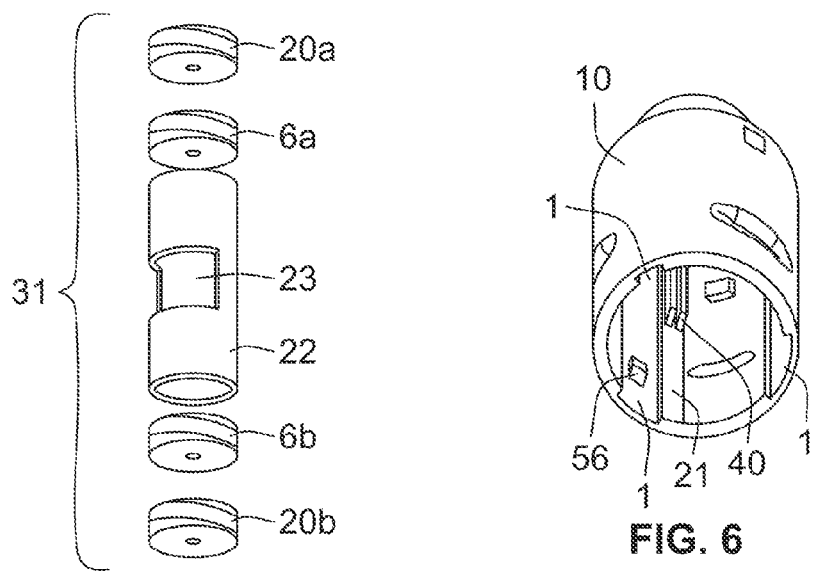
FIG. 5
FIG. 6

MEDICATED MODULE WITH AUTOMATIC RESERVOIR ENGAGEMENT

CROSS REFERENCE TO RELATED APPLICATIONS

The present application is a 35 U.S.C. 371 National Application of PCT/EP2011/054426 filed Mar. 23, 2011 and claims priority to U.S. Patent Application No. 61/317,548, filed Mar. 25, 2010, and U.S. Patent Application No. 61/331,911, filed May 6, 2010, and European Patent Application No. 10170281.9, filed Jul. 21, 2010 and European Patent Application No. 10170284.3, filed Jul. 21, 2010, the entire contents of which are incorporated entirely herein by reference.

FIELD OF THE PRESENT DISCLOSURE

Specific embodiments of this disclosure relate to medical devices and methods of delivering at least two drug agents from separate reservoirs using devices having only a single dose setting mechanism and a single dispense interface. A single delivery procedure initiated by the user may cause a non-user settable dose of a second drug agent or secondary medicament and a variable set dose of a first drug agent or primary medicament to be delivered to the patient. The drug agents may be available in two or more reservoirs, containers or packages, each containing independent (single drug compound) or pre-mixed (co-formulated multiple drug compounds) drug agents. Specifically, the present disclosure concerns a medicated module where the user does not have to manually select or set the module in order to dispense the second drug agent. Activation of the needle guard may automatically cause the reservoir of secondary medicament to engage with dispensing conduits to allow a set dose of the primary medicament and a single fixed dose of the of the secondary medicament to be injected. The present disclosure is of particular benefit where the therapeutic response can be optimized for a specific target patient group, through control and definition of the therapeutic profile.

BACKGROUND

Certain disease states require treatment using one or more different medicaments. Some drug compounds need to be delivered in a specific relationship with each other in order to deliver the optimum therapeutic dose. The present disclosure is of particular benefit where combination therapy is desirable, but not possible in a single formulation for reasons such as, but not limited to, stability, compromised therapeutic performance and toxicology.

For example, in some cases it might be beneficial to treat a diabetic with a long-acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems when delivering two medicaments or active agents simultaneously. The two active agents may interact with each other during the long-term, shelf life storage of the formulation. Therefore, it is advantageous to store the active components separately and only combine them at the point of delivery, e.g. injection, needle-less injection, pumps, or inhalation. However, the process for combining the two agents needs to be simple and convenient for the user to perform reliably, repeatedly and safely.

A further problem is that the quantities and/or proportions of each active agent making up the combination therapy may need to be varied for each user or at different stages of their therapy. For example, one or more actives may require a titration period to gradually introduce a patient up to a "maintenance" dose. A further example would be if one active requires a non-adjustable fixed dose while the other one is varied in response to a patient's symptoms or physical condition. This problem means that pre-mixed formulations of multiple active agents may not be suitable as these pre-mixed formulations would have a fixed ratio of the active components, which could not be varied by the healthcare professional or user.

Additional problems may arise where a multi-drug compound therapy is required, because many users cannot cope with having to use more than one drug delivery system or to make the necessary accurate calculation of the required dose combination. This is especially true for users with dexterity or computational difficulties. In some circumstances it may also be necessary to perform a priming procedure of the device and/or needle cannulae before dispensing the medicaments. Likewise, in some situations, it may be necessary to bypass one drug compound and to dispense only a single medicament from a separate reservoir.

Accordingly, there exists a strong need to provide devices and methods for the delivery of two or more medicaments in a single injection or delivery step that is simple for the user to perform. The present disclosure may overcome the above-mentioned problems by providing separate storage containers for two or more active drug agents that are then only combined and/or delivered to the patient during a single delivery procedure. Setting a dose of one medicament may automatically fix or determine the dose of the second (i.e. non-user settable). Medicament. The present disclosure may also give the opportunity for varying the quantity of one or both medicaments. For example, one fluid quantity can be varied by changing the properties of the injection device (e.g. dialing a user variable dose or changing the device's "fixed" dose). The second fluid quantity can be changed by manufacturing a variety of secondary drug containing packages with each variant containing a different volume and/or concentration of the second active agent. The user or healthcare professional would then select the most appropriate secondary package or series or combination of series of different packages for a particular treatment regime.

The present disclosure also provides a medicated module that may automatically cause the reservoir of the secondary medicament to come into fluid communication with the primary medicament upon activation of the needle guard. This eliminates the need for the user to manually set or adjust the medicated module after performing a priming step.

These and other advantages will become evident from the following more detailed description of the invention.

Problem to be Solved

The problem to be solved by the present invention is to provide a medicated module and a drug delivery system where the safety for the user is improved.

SUMMARY

The present disclosure allows complex combinations of multiple drug compounds within a single drug delivery system. The disclosure allows the user to set and dispense a multi-drug compound through one single dose setting mechanism and a single dispense interface. This single dose setter may control the mechanism of the device such that a predefined combination of the individual drug compound is delivered when a single dose of one of the medicaments is set and dispensed through the single dispense interface.

By defining the therapeutic relationship between the individual drug compounds the disclosed delivery device may help to ensure that a patient/user receives the optimum therapeutic combination dose from a multi-drug compound device without the inherent risks associated with multiple inputs where the user has to calculate and set the correct dose combination every time he uses the device. The medicaments can be fluids, defined herein as liquids or powders that are capable of flowing and that change shape at a steady rate when acted upon by a force tending to change its shape. Alternatively, one of the medicaments may be a solid that is carried, solubilized or otherwise dispensed with another fluid medicament.

According to one specific aspect, the present disclosure is of particular benefit to users with dexterity or computational difficulties as the single input and associated predefined therapeutic profile may remove the need for them to calculate their prescribed dose every time they use the device and the single input allows considerably easier setting and dispensing of the combined compounds.

In a preferred embodiment, a master or primary drug compound, such as insulin, contained within a multiple dose, user selectable device could be used with a single use, user replaceable, module that contains a single dose of a secondary medicament and the single dispense interface. When connected to the primary device, the secondary compound may be activated/delivered on dispense of the primary compound. Although the present disclosure specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with the drug delivery system and the medicated module of the present disclosure.

For the purposes of our invention the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys(B3), Glu(B29) human insulin; Lys(B28), Pro (B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH2).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

One aspect relates to a medicated module. The medicated module may be, preferably releasably, attachable to a drug delivery device. The medicated module may comprise a reservoir containing a medicament. The medicated module may comprise a medicated needle, i.e. a needle containing a medicament. The medicated module may comprise a proximal needle cannula. The medicated module may comprise a distal needle cannula. The medicated module may comprise the needle cannulae before it is attached to the device.

The drug delivery device may be suitable to perform a dose setting and/or dose delivery operation for setting and/or delivering a dose of the first medicament when the device is not connected with the medicated module.

The medicated module may comprise an outer housing. The outer housing may comprise at least one needle cannula. The needle cannula may be a double-ended needle cannula, for example. The medicated module may comprise a needle guard. The needle guard may be configured to provide protection of the needle cannula. The medicated module may comprise a coupling member. At least one track may be provided on an outer surface of the coupling member. The coupling member may be adapted and arranged to mechanically cooperate with the needle guard, in particular the coupling member may be configured to releasably or permanently couple the needle guard. The coupling member may be a sleeve. The coupling member may be arranged within the outer housing. The medicated module may comprise a reservoir. The reservoir may be provided within the coupling member. The reservoir may be provided within the coupling member before the medicated module is attached to the device. The reservoir may comprise a medicament, preferably a single dose of the medicament. The needle guard may comprise at least one drive tooth. The drive tooth and the needle guard may be formed unitarily. The drive tooth may be provided on an inner surface of the needle guard. The at least one drive tooth may be configured to mechanically cooperate with the coupling member, in particular with the at least one track provided on the outer surface of the coupling member. In particular each drive tooth may be configures to mechanically cooperate with one respective track.

There is provided the medicated module attachable to the drug delivery device, e.g. a pen-type device. The medicated module may comprise an outer housing having a proximal end, a distal end, and an outer surface, where the proximal end may comprise a hub, e.g. an upper hub, holding the, preferably double-ended, needle. The housing may comprise a connector configured for attachment to a drug delivery device. There is the reservoir in the coupling member provided within the outer housing that contains the medicament. The medicated module assembly contains the needle guard that can reduce the risk of accidental needle sticks before and after use, reduce the anxiety of users suffering from needle phobia as well as preventing a user from using the device a subsequent time when the additional medicament has already been expelled.

According to an embodiment, the medicated module comprises a lower hub. The lower hub may be configured to be, permanently or releasably, engaged with the coupling member. Furthermore, the lower hub may be configured to be, permanently or releasably, engaged with the needle guard. The lower hub may be configured to hold a further needle cannula, e.g. a double ended needle cannula.

According to an embodiment, the needle guard is axially moveable with respect to the housing between an extended and a retracted position. The medicated module may comprise a biasing member, e.g. a spring. The biasing member may be configured to bias the needle guard towards the extended, e.g. the distal, position.

According to an embodiment, the biasing member is configured to mechanically cooperate with, in particular to be engaged between, an internal proximal face of the needle guard and the lower hub. The biasing member may be adapted and arranged to exert a force onto the lower hub when the needle guard is pushed in the proximal direction causing the lower hub and the coupling member to move in the proximal direction. Accordingly, the reservoir may be caused to come into fluid communication with the needle cannulae.

According to an embodiment, the track provided on the coupling member comprises a first path. The track may comprise a second path. The track may comprise a third path. The track may comprise a fourth path. The paths may form a continuous track system on the coupling member.

According to an embodiment, the at least one drive tooth is configured to mechanically cooperate with the first, second, and third paths of the respective track during retraction and partial extension of the needle guard. The drive tooth may be configured further to mechanically cooperate with the fourth path during final extension of the needle guard into a locking position. In the locking position, the needle guard may be fully extended in a post-use position. In the post-use position, the needle guard may be configured to be prevented from further axial movement with respect to the housing.

The needle guard is preferably configured with a solid planar surface at its distal end that provides a large surface area that reduces the pressure exerted on the patient's skin, which allows the user to experience an apparent reduction in the force exerted against the skin. Preferably, the planar surface covers the entire distal end of the needle guard with the exception of a small needle pass through hole aligned axially with the needle. This pass through hole is preferably no more than 10 times greater in diameter than the outer diameter of the needle cannula. For example, with a needle outside diameter of 0.34 mm, the pass through hole diameter D can be 3.4 mm. Preferably, the pass through hole size should be large enough for the user to see that the device is primed, e.g. the user may see a drop or more of medicament, while not being so large that it is still possible to reach the end of the needle with a finger, i.e. needle stick injuries before or after use may be prevented. This difference between the hole size and cannula diameter is to allow for tolerances, to allow users to see the drop of liquid on the end of the cannula after priming (whether a transparent or non-transparent guard is used) while keeping the size small enough to prevent accidental needle stick injuries.

Further, the movable needle guard or shield may be configured to move axially in both the distal and proximal directions when pressed against and removed from an injection site. When the medicated module is removed or withdrawn from the patient, the needle guard may be returned to the post-use extended position. The drive tooth on the inside surface of the guard may engage a stop on the track on the outer surface of the coupling member to securely lock the needle guard from further substantial axial movement. Preferably, a lock out boss on the outer surface of the coupling member is configured to engage a lock out feature on the inner proximal surface of the outer housing at the completion of the injection to further lock the medicated module from any further use and prevent the needle(s) and/or bypass component from being able to substantially move within the system even if the needle guard is held in an axially locked condition. By "substantial" movement we do not mean the typical amount of "play" in a system, but instead we mean that the guard and/or distal needle do not move axially a distance that exposes the distal end of the cannula once it is locked out.

One goal of the present disclosure is to eliminate the need to have the user manually operate the medicated module to change the state of the module from a priming state to a combination dose delivery state. Manually operated devices are sometimes not as intuitive as they could be and raise the risk of accidental misuse. The present disclosure may solve this problem by utilizing energy stored within the medicated module prior to delivery of the device to the user. The stored energy can come from the biasing member, such as the compressed spring. This stored energy may be released during normal user operation of the medicated module by actuating the mechanism and, thus, activating the state change from prime dose to combination dose. The mechanism aims to make this actuation imperceptible to the user, consequently making the user experience of the medicated module very similar to that of a standard commercially available and accepted needle or safety needle assembly (i.e. unpack module, attach to a drug delivery device, prime drug delivery device, inject a set dose along with single dose in the module). In this way, the module mechanism aims to reduce the risk of unintentional misuse and to improve usability by replicating an already accepted practice for similar injection methods.

According to an embodiment, the coupling member comprises a lower stand off pocket. The lower stand off pocket may be configured to mechanically cooperate with legs provided on the lower hub. The coupling member may comprise an upper stand off pocket. The upper stand off pocket may be configured to mechanically cooperate with a radial stand off provided on the housing. Accordingly, movement of the coupling member and the lower hub in the proximal direction with respect to the housing may be prevented when the at least one drive tooth mechanically travels along the first path as the needle guard moves proximally.

According to an embodiment, movement of the drive tooth from the first path into the second path is configured to disengage the upper stand off pocket from the radial stand off. Accordingly, proximal movement of the coupling member and the lower hub may be allowed for establishing fluid communication of the reservoir and the needle cannulae. As the medicated module mechanism does not require the user to access external features on the medicated module for the purposes of actuation, the number of components and subsequent module size can be reduced/optimized. These factors make the mechanism ideal for a single-use, high-volume manufacture, and disposable device application. Alternatively, as the actuation is driven by a single energy store, the system lends itself to a resettable actuation mechanism. The preferred embodiment described below is the single use (non-resettable) version. The lower hub is preferably restrained rotationally with regard to the needle guard, but may be free to move axially within the needle guard. The needle guard may be restrained rotationally with regard to the outer housing, but may be free to move axially, between defined constraints, within the outer housing.

According to an embodiment, the needle guard is, preferably permanently, rotationally constrained by the housing. The coupling member may be rotationally constrained when the at least one drive tooth mechanically cooperates with the second or third paths of the track. The medicated module may be configured to provide an audible and/or tactile indication to a user when the coupling member rotates as the at least one drive tooth moves from the second path to the third path as the needle guard moves proximally.

According to an embodiment, the housing comprises one or more openings. The at least one opening may be configured for viewing indicia. Said indicia may be provided on an outer surface of the needle guard or of the coupling member. The indicia may be configured to indicate one or more of a pre-use position, a triggered state, where the reservoir is in fluid communication with needle cannulae, or a locked position where the needle guard is in the post-use position. Preferably, the housing comprises three openings or windows, one respective window for one indicia, e.g. for indicating one respective state of the needle guard.

The user pressing the distal face of the needle guard against the skin may cause axial motion of the needle guard in the proximal direction. This axial motion of the guard may cause rotation of the coupling member through the engagement and action of an inward-facing drive tooth on the needle guard as it travels in the track having the one or more paths, which track is located on the outer surface of the coupling member. After sufficient axial travel of the needle guard, the rotation of the coupling member brings stand-offs inside the outer housing and at the proximal ends of the lower hub into line with the previously described pockets located on the outer surface of the coupling member. Alignment of the stand-offs with the pockets allows the coupling member to move axially in the proximal direction and further into the outer housing. The lower hub containing the double-ended needle cannula moves axially further onto the coupling member. Both of these movements occur due to the relaxation/release of the stored energy of the biasing member, preferably a spring that is pre-compressed during module assembly or manufacture, and constitute "triggering" of the actuation mechanism. It is this axial movement of the lower hub onto the coupling member and the corresponding movement of the coupling member further into the outer body that results in the, preferably double ended, needles located in the outer body distal end and the lower hub piercing the medicated module, moving it from a state of priming to combination dose delivery.

Further axial movement of the needle guard is required in order to pierce the skin, this retraction of the needle guard may temporarily re-compress the biasing member creating additional stored energy. At a "commit" point, the proximal axial movement of the drive tooth may pass a non-return feature in the track through further rotation of the coupling member. In normal use, once the drug has been dispensed and the needle is removed from the skin, the needle guard may be allowed to return axially in the distal direction under the relaxation of the biasing member as it releases its stored energy. At some point along its return travel, the drive tooth may contact a further ramped face in one of the paths of the track, resulting in yet further rotation of the coupling member. At this point, the outer housing stand-off may come into contact with a ramp feature on the outer surface of the coupling member. The combination of this feature with the ramp between the drive tooth and the coupling member track may result in further biasing of the coupling member stop face into the needle guard drive tooth. The stop face features may act as an axial locking pocket. The action of the combined biasing force means that any axial load in the proximal direction put on the needle guard may result in the tooth being stopped in this pocket, locking out the needle guard from further use or exposing the needle. Should the user remove the device from the skin without dispensing fluid, but after the "commit" point has been passed, the needle guard would return to an extended position and lock out as previously described.

According to an embodiment, there is provided a medicated module assembly attachable to a drug delivery device, preferably a pen shaped injection device, where the medicated module assembly comprises an outer housing having a proximal end and a distal end, where the proximal end has an upper hub holding a first double-ended needle cannula and a connector configured for attachment to a drug delivery device. The hub can be a separate part from the housing or integral, for example molded as part of the housing. The connector can be any connector design, such as threads, snap fits, bayonet, lure lock, or combination of these designs.

Two needle cannula are used, a distal cannula and a proximal cannula, with both cannulae preferably being doubled-ended for piercing a septum or seal and for piercing skin. The distal needle may be mounted in the lower hub and the proximal needle may be mounted in the upper hub, each using any technique known to those skilled in the art, such as welding, gluing, friction fit, over-molding and the like. The medicated module assembly may also contain the previously described biasing member, preferably a compression spring. The biasing member is preferably in a pre-compressed state and positioned between the proximal inner face of the needle guard and the distal face of the lower hub. Although a preferred biasing member is a spring, any type of member that produces a biasing force will work. The spring could also be torsion or tension spring The biasing member may also be assembled in an energized state and positioned between the proximal inner face of the needle guard and the distal face of the lower hub. For a compression spring, this would mean that the spring is assembled into the device pre-compressed, within an axial space shorter than its free length.

According to an embodiment, the coupling member may comprise a bypass channel. The bypass channel may be arranged on an inner surface of the coupling member. The bypass channel may be configured to allow a dose of the primary medicament contained in the drug delivery device to bypass the reservoir when the needle guard is in the pre-use position before fluid communication is established between the reservoir and the needle cannulae.

The medicated module assembly may automatically, once triggered, change state from (1) a pre-use or priming state, where a small amount of primary medicament may flow in the bypass channel around the reservoir containing a single dose of the secondary medicament, to (2) the ready-to-use or combination dose state, where both the upper and lower cannulae are in fluid engagement with the fixed dose of the secondary medicament within the module and where a set dose of the primary medicament can be injected along with the non-settable single dose of secondary medicament in the reservoir, and finally to (3) the locked out state, where the needle guard is prevented from substantial proximal movement. The outer housing preferably has the previously described opening or window or indicator that shows the various states of the module. The indicator can be a pip, knob, button, or the like that protrudes through the outer surface of the proximal end of the needle guard and visually shows the user whether the module is in the pre-use or ready-to-use state. It may also be a visual indicator, e.g. showing colors or symbols, or a tactile or audible indicator. Preferably, user noticeable indicia indicate both the pre-use priming position and the locked position of the guard after the medicated module assembly has been used to perform an injection.

According to an embodiment, the reservoir is a single molded component having an internal cavity with an integral flow distributor. The flow distributor may be configured to guide flow of a fluid, e.g. a primary medicament held in the device, to help expelling the medicament, in particular substantially all of the medicament, e.g. at least about 90% of the medicament, from the reservoir.

According to an embodiment, the reservoir contains a liquid medicament. The medicament in the capsule may comprise a GLP-1. Alternatively, the medicament in the capsule may comprise a premix of insulin and a GLP-1.

Inside the coupling member there is a cavity that contains the capsule, which comprises the single dose of medicament in the reservoir. As the needle guard is retracted during an injection, the coupling member is moved proximally along with the capsule positioned inside the cavity, thus decreasing the cavity volume. This may allow the seals of the capsule to be pierced at its top and bottom by the needle cannulae such that the medicament can be expelled from the reservoir during dose delivery. When connected to a drug delivery device containing a primary medicament and prior to piercing the seals of the reservoir, the needle cannulae are only in fluid communication with the primary medicament and the fluid flow path that bypasses the capsule. Preferably, a channel on the inside surface of the coupling member is part of this fluid flow path and is used in the priming function of the drug delivery device. This may allow the primary device to be primed through the medicated module without dispensing the contents of the medicament reservoir inside the medicated module.

As mentioned, the coupling member preferably has one or more tracks located on the outside surface each having a set of first, second, third, and fourth paths. On the inner surface of the proximal end of the needle guard one or more radial protrusions or drive teeth may be provided. As the guard first begins to retract, these protrusions may travel in the first path causing the coupling member to slightly rotate. As the guard continues to retract and then partially extend, the protrusions may travel in the second and third paths. The protrusion may move to the fourth path and into a locking position when the guard is fully extended to its post-use position, which is preferably less extended than the starting position. This different position may be used to provide an indication that the device has been used. The needle guard may be, as mentioned above, rotationally constrained by the outer housing, preferably by the use of one or more spline features, e.g. one or more grooves, provided in the outer surface of the needle guard in cooperation with one or more followers or pips located at the distal end of the inner surface of the outer housing. The coupling member may be, as mentioned above, rotationally constrained when the protrusion is in the second path of the track. As the protrusion is moved axially in the proximal direction when the guard retracts, the protrusion may move from the second track to the third track causing the assembly to emit the previously mentioned audible sound and/or tactile feedback. This may tell the user that the device will now have been activated to lock upon extension of the needle guard in the distal direction.

One aspect relates to a drug delivery system. The drug delivery system may be configured to deliver two or more medicaments. The drug delivery system may be operable through a single dispense interface, e.g. a needle cannula. The drug delivery system may comprise a primary reservoir of medicament. The primary reservoir may contain at least one primary medicament, in particular a plurality of doses of the primary medicament. The drug delivery system may comprise a single dispense interface. The dispense interface may be configured for fluid communication with the primary reservoir. The drug delivery system may comprise the previously described medicated module. The single dispense interface may be part of the medicated module.

According to an embodiment, the primary medicament is configured to flow via the bypass channel and through the single dispense interface when the needle guard is in the pre-use position. Mechanical cooperation of the needle guard with the second path of the coupling member may be configured to enable the medicament in the reservoir to be dispensed along with the primary medicament through the single dispense interface.

According to an embodiment, the drug delivery system comprises a dose button. The dose button may be permanently or releasably operably connected to the primary reservoir of medicament. Activation of the dose button may cause the primary medicament to be dispensed through the single dispense interface.

A further aspect relates to a method of dispensing a fixed dose of one medicament and a variable dose of a primary medicament from separate reservoirs. The method may involve the steps of first attaching a medicated module to a delivery device, the medicated module being set in a pre-use or prime only state as described above. The user can prime the dose delivery device using only the primary medicament and bypassing the secondary medicament. After priming, the user may begin the injection and the needle guard begins to retract, the module automatically changing to second state that may allow a combination delivery of the two medicaments. Upon completion of the delivery procedure and retraction of the needle from the injection site, the extension of the needle guard may automatically change the module to a third state, e.g. the locked state.

During dispense, substantially the entire amount of secondary medicament may have been expelled as well as the selected or dialed dose of the primary medicament, through the single dispense interface. The capsule preferably contains the flow distributor which helps to expel substantially all the single dose of secondary medicament out of the capsule by the primary medicament during an injection. The flow distributor can be a separate stand alone insert or pin. Alternatively, the flow distributor and the capsule together can be manufactured or assembled as a one-piece component where the flow distributor is integral with the capsule. Such a unitary construction can be achieved utilizing, for example, design principles such as form fit, force fit or material fit, such as welding, gluing, or the like, or any combination thereof. The one-piece component may comprise one or more medicament flow channels, preferably one flow channel. The capsule and/or flow distributor can be constructed of any material that is compatible to the primary and secondary medicaments. Preferably, the capsule and/or flow distributor can be made from compatible materials of construction that include, but are not limited to, COC (an amorphous polymer based on ethylene and norbonene, also referred to as cyclic olefin copolymer, ethylene copolymer, cyclic olefin polymer, or ethylene-norbornene copolymer), LCP (a liquid crystal polymer having an aramid chemical structure that includes linearly substituted aromatic rings linked by amide groups, and further can include partially crystalline aromatic polyesters based on p-hydroxybenzoic acid and related monomers and also highly aromatic polyesters), PBT (polybutylene terephthalate thermoplastic crystalline polymer or polyester), COP (a cyclic olefin polymer based on ring-opening polymerization of norbornene or norbornene-derivatives), HDPE (high density polyethylene), and SMMA (styrene methyl methacrylate copolymer based on methyl methacrylate and styrene). A preferred material is one that is typically used to manufacture septa or pistons (bungs) found in multi-dose medicament cartridges, however, any other material that is compatible with the drug could be used, e.g. glass, plastics or specific polymers, for example, TPE (thermo plastic elastomer), LSR (liquid silicone rubber), LDPE (low density polyethylene), and/or any kind of medical grade rubber, natural or synthetic. By "substantially all" it is meant that at least about 80% of the secondary medicament is expelled from the drug delivery device, preferably at least about 90% is expelled. In the third state, preferably the module is locked so as to prevent a second delivery or insertion by means of a locking mechanism as described previously.

The combination of compounds as discrete units or as a mixed unit may be delivered to the body via an integral needle. This would provide a combination drug injection system that, from a user's perspective, would be achieved in a manner that very closely matches the currently available injection devices that use standard needles.

The medicated module can be designed for use with any drug delivery device with an appropriate compatible interface. However, it may be preferable to design the module in such a way as to limit its use to one exclusive primary drug delivery device (or family of devices) through employment of dedicated/coded/exclusive features to prevent attachment of a non-appropriate medicated module to a non-matching device. In some situations, it may be beneficial to ensure that the medicated module is exclusive to one drug delivery device while also permitting the attachment of a standard drug dispense interface to the device. This would allow the user to deliver a combined therapy when the module is attached, but would also allow delivery of the primary compound independently through a standard drug dispense interface in situations, such as, but not limited to, dose splitting or top-up of the primary compound.

A particular benefit is that the medicated module makes it possible to tailor dose regimes when required, especially where a titration period is necessary for a particular drug. The medicated module could be supplied in a number of titration levels with obvious differentiation features such as, but not limited to, aesthetic design of features or graphics, numbering etc, so that a patient could be instructed to use the supplied medicated module in a specific order to facilitate titration. Alternatively, the prescribing physician may provide the patient with a number of "level one" titration medicated modules and then, when these were finished, the physician could prescribe the next level. A key advantage of this titration program may be that the primary device remains constant throughout.

According to a preferred embodiment, a medicated module attachable to a drug delivery device is provided, the medicated module comprising an outer housing, the outer housing comprising at least one needle cannula. The medicated module comprises a needle guard configured to provide protection of the needle cannula. The medicated module comprises a coupling member adapted and arranged to mechanically cooperate with the needle guard. The medicated module comprises a reservoir provided within the coupling member, the reservoir comprising a single dose of a medicament. The needle guard comprises at least one drive tooth provided on an inner surface of the needle guard, wherein the drive tooth is configured to mechanically cooperate with a track provided on an outer surface of the coupling member.

According to a preferred embodiment, a medicated module attachable to a drug delivery device is provided, the medicated module comprising an outer housing having an inner surface, a proximal end and a distal end, where the proximal end has an upper hub holding a first double-ended needle cannula and a connector configured for attachment to a drug delivery device. The medicated module further comprises a bypass housing having an outer surface and being slidably engaged with an upper radial stand off on the inner surface of the housing. The medicated module further comprises a reservoir within the bypass housing comprising a single dose of a medicament and a guard having an internal proximal face and a drive tooth on an inner surface, where the drive tooth is slidably engaged with a track on the outer surface of the bypass housing. The medicated module further comprises a lower hub slidably engaged with the outer surface of the bypass housing and slidably engaged with the inner surface of the needle guard and a biasing member engaged between the internal proximal face of the guard and with the lower hub.

The bypass housing may be arranged within the outer housing. The bypass housing may form an inner housing of the medicated module. The bypass housing may form a coupling member. In particular, the bypass housing may be configured to mechanically cooperate with, in particular to couple with, the needle guard. A bypass channel may be arranged within the bypass housing which enables, in an unprimed state of the device, fluid communication of the cannula with a primary medicament held in the drug delivery device.

According to a preferred embodiment, a drug delivery system is provided which is configured to deliver two or more medicaments operable through a single dispense interface. The drug delivery system comprises a primary reservoir of medicament containing at least one primary medicament, a single dispense interface configured for fluid communication with the primary reservoir and the previously described medicated module.

According to a preferred embodiment, a drug delivery system is provided to deliver two or more medicaments operable through a single dispense interface, the drug delivery system comprising a primary reservoir of medicament containing at least one drug agent, a dose button operably connected to the primary reservoir of medicament and a single dispense interface configured for fluid communication with the primary reservoir. The drug delivery system further comprises a medicated module comprising an outer housing having an inner surface, a proximal end and a distal end, where the proximal end has an upper hub holding a first double-ended needle cannula and a connector configured for attachment to a drug delivery device. The medicated module further comprises a bypass housing having an outer surface and slidably engaged with an upper radial stand off on the inner surface of the housing and a reservoir within the bypass housing comprising a single dose of a medicament. The medicated module further comprises a guard having an internal proximal face and a drive tooth on an inner surface, where the drive tooth is slidably engaged with a track on the outer surface of the bypass housing. The medicated module further comprises a lower hub slidably engaged with the outer surface of the bypass housing and slidably engaged with the inner surface of the needle guard and a biasing member engaged between the internal proximal face of the guard and with the lower hub.

In a preferred embodiment, the primary drug delivery device is used more than once and therefore is multi-use, however, the drug delivery device may also be a single use disposable device. Such a device may or may not have a replaceable reservoir of the primary drug compound, but the drug delivery system of the present disclosure is equally applicable to both scenarios. It is also possible to have a suite of different medicated modules for various conditions that could be prescribed as one-off extra medication to patients already using a standard drug delivery device. Should the patient attempt to reuse a previously used medicated module, the present disclosure includes the locking needle guard that is activated after a first predefined travel/retraction of the guard/insertion of the needle. The locked needle guard would alert the patient to this situation and the medicated module would be unable to be used for a second time. Visual warnings (e.g. change in color and/or warning text/indicia within an indication window on the module once insertion and/or fluid flow has occurred) can also be used. Additionally, tactile feedback (presence or absence of tactile features on the outer surface of the module hub following use) could be used as well.

A further feature is that both medicaments may be delivered via one injection needle and in one injection step. This may offer a convenient benefit to the user in terms of reduced user steps compared to administering two separate injections. This convenience benefit may also result in improved compliance with the prescribed therapy, particularly for users who find injections unpleasant or who have computational or dexterity difficulties.

The present disclosure also covers the method of delivering two medicaments stored in separate primary packages. The medicaments may both be liquid, or alternatively, one or more of the medicaments may be a powder, suspension or slurry. In one embodiment, the medicated module could be filled with a powdered medicament that is either dissolved or entrained in the primary medicament as it is injected through the medicated module.

These as well as other advantages of various aspects of the present invention will become apparent to those of ordinary skill in the art by reading the following detailed description, with appropriate reference to the accompanying drawings.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE DRAWINGS

Exemplary embodiments are described herein with reference to the drawings, in which:

FIG. 4 illustrates an exploded proximal perspective view of all the components (except the medicated capsule) of the medicated module illustrated in FIG. 2;

FIG. 5 is a perspective view of the capsule containing the reservoir of the medicated module of FIG. 2;

FIG. 6 illustrates a proximal perspective view of the outer housing of the medicated module of FIG. 2;

DETAILED DESCRIPTION

Figure 1:
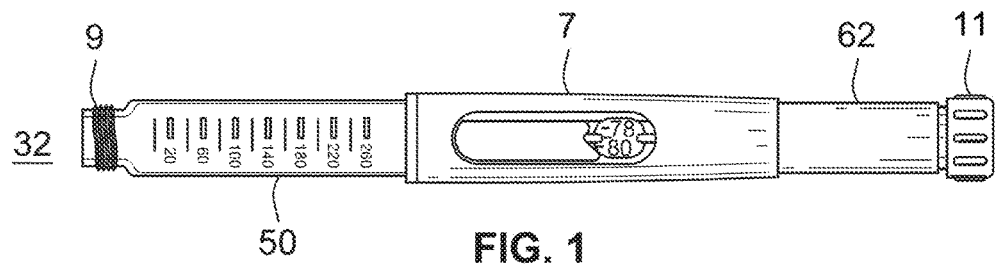
FIG. 1 illustrates one possible drug delivery device that can be used with the medicated module of the present disclosure.

In the present disclosure, a fixed predetermined dose of a secondary drug compound (secondary medicament) and a variable dose of a primary or first drug compound (primary medicament) may be administered through a single output or drug dispense interface. Setting the dose of the primary medicament by the user may automatically determine the fixed dose of the secondary medicament, which preferably is a single dose contained in a capsule or reservoir having an integral flow distributor. In a preferred embodiment, the drug dispense interface is a needle cannula (hollow needle). FIG. 1 illustrates one example of a drug delivery device 7 that the medicated module 4 (see FIG. 2 or 7) can be attached to. The medicated module 4 may be attached to a connection means 9 provided on a cartridge holder 50 of distal end 32 of the device 7. Each medicated module 4 is preferably self-contained and provided as a sealed and sterile disposable module that has an attachment means 8 (see FIG. 7) compatible to the attachment means 9 at the distal end 32 of device 7. Although not shown, the medicated module 4 could be supplied by a manufacturer in a protective and sterile container, where the user would peel or rip open a seal or the container itself to gain access to the sterile medicated module 4. In some instances, it might be desirable to provide two or more seals for each end of the medicated module 4.

Figure 2:
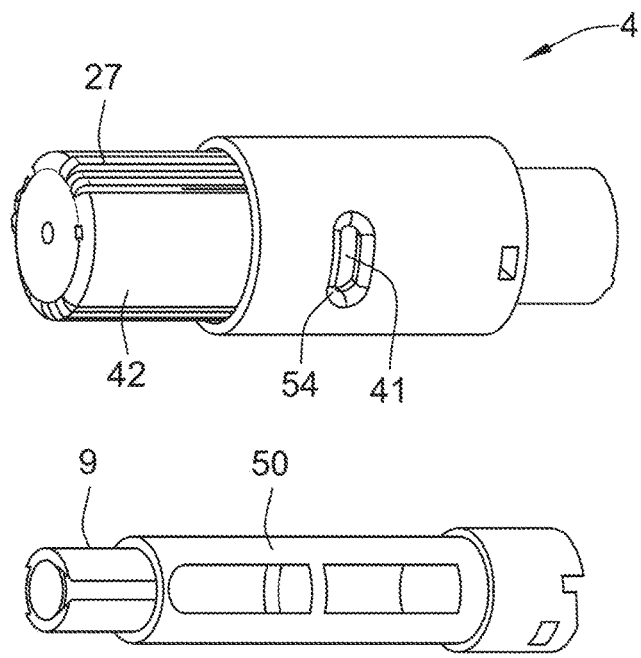
FIG. 2 illustrates an embodiment of the medicated module, where the medicated module is separated from an attachable cartridge holder of the drug delivery device.
Figure 7:
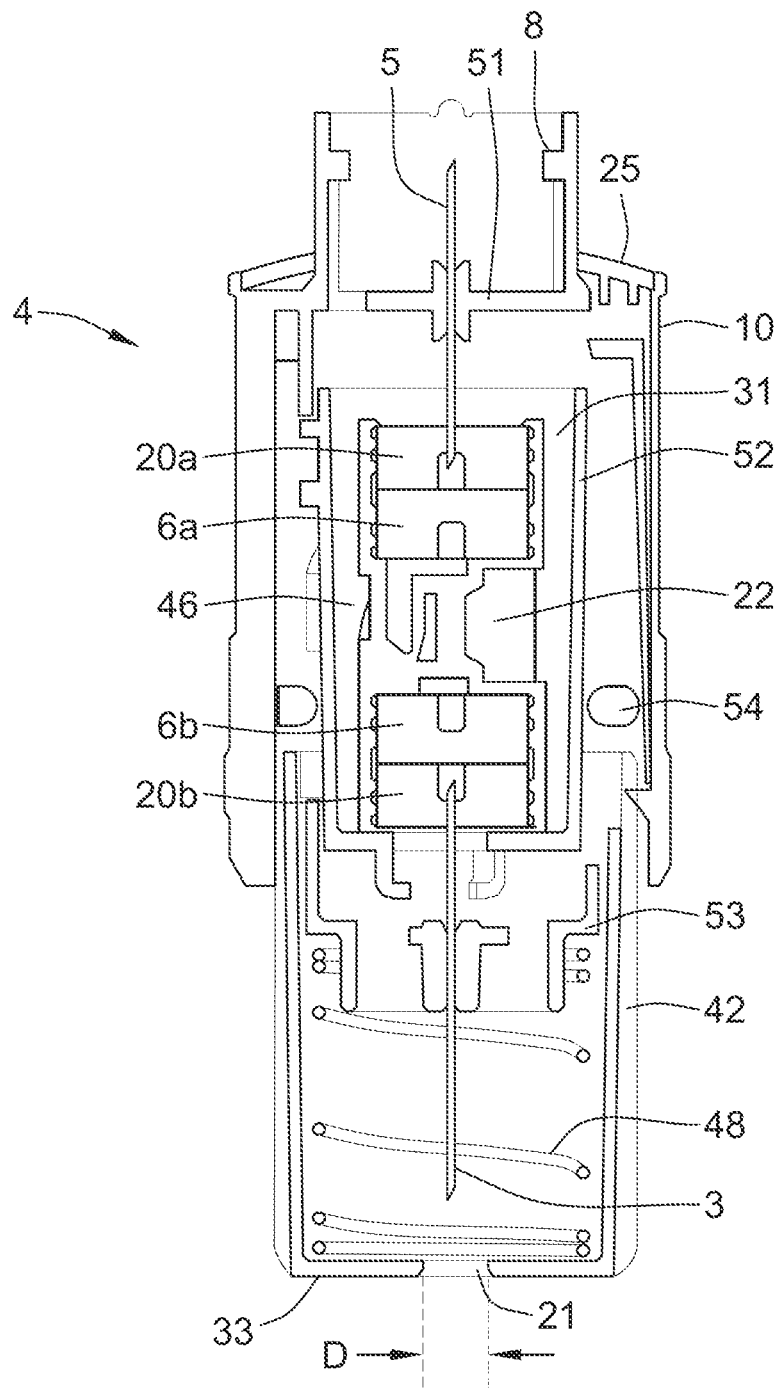
FIG. 7 is a sectioned view of the embodiment of the medicated module shown in FIG. 2 orientated in a bypass configuration.

Any known attachment means 8 can be used to attach the medicated module 4 to the chosen drug delivery device 7, including all types of permanent and removable connection means, such as threads, snap locks, snap fits, luer locks, bayonet, snap rings, keyed slots, and combinations of such connections. FIGS. 2, 4, and 7 illustrate the attachment means 9 as a unique bayonet type connection that is keyed specifically to a corresponding female bayonet type connection 8 on a upper hub 51 of medicated module 4. The embodiments shown in FIGS. 2, 4, 5, and 7 have the benefit of the secondary medicament as a single dose being contained entirely within a capsule 31, and specifically in a reservoir 22, hence minimizing the risk of material incompatibility between the secondary medicament and the materials used in the construction of the medicated module 4, specifically housing 10, inner housing or coupling member 52, or any of the other parts used in the construction of the medicated module 4.

To minimize the residual volume of the secondary medicament, caused by recirculation and/or stagnant zones, that might remain in capsule 31 at the end of the dispense operation, it is preferable to have a flow distributor 23 as an integral part of reservoir 22 (see FIG. 5). The reservoir 22 containing the single dose of the secondary medicament can be sealed with septa 6a and 6b, which are fixed to the capsule using keepers or plugs 20a and 20b. Preferably, the keepers 20a, 20b have fluid channels that are in fluid communication with needles 3 and 5 and with a bypass 46, which is preferably part of the inside surface of coupling member 52. Together this fluid path allows priming of the drug delivery device 7 before injection. Preferably the reservoir 22, flow distributor 23, keepers 20a, 20b, and bypass 46 can be made from materials that are compatible with the primary medicament. Examples of compatible materials of construction include, but are not limited to, COC (an amorphous polymer based on ethylene and norbonene, also referred to as cyclic olefin copolymer, ethylene copolymer, cyclic olefin polymer, or ethylene-norbornene copolymer); LCP (a liquid crystal polymer having an aramid chemical structure that includes linearly substituted aromatic rings linked by amide groups, and further can include partially crystalline aromatic polyesters based on p-hydroxybenzoic acid and related monomers and also highly aromatic polyesters); PBT (polybutylene terephthalate thermoplastic crystalline polymer or polyester); COP (a cyclic olefin polymer based on ring-opening polymerization of norbornene or norbornene-derivatives); HDPE (high density polyethylene); and SMMA (styrene methyl methacrylate copolymer based on methyl methacrylate and styrene). The needle pierceable septa, bungs, and/or seals that are used with both the capsule and the primary medicament cartridge can be manufactured using TPE (thermo plastic elastomer); LSR (liquid silicone rubber); LDPE (low density polyethylene); and/or any kind of medical grade rubber, natural or synthetic.

The design of flow distributor 23 may help to expel at least about 80% of the secondary medicament from reservoir 22 through the distal end of needle 3. Most preferably, at least about 90% should be expelled. Ideally, displacement of the primary medicament in the primary reservoir (not shown) contained in cartridge holder 50 and through the capsule 31 will displace the single dose of the secondary medicament stored in reservoir 22 without substantial mixing of the two medicaments.

Attachment of the medicated module 4 to the multi-use device 7 causes proximal needle 5 to penetrate a septum (not shown) sealing the distal end of the cartridge of primary medicament positioned in cartridge holder 50 of the multi-use device 7. Once the needle 5 has passed through the septum of the cartridge, fluid connection is made between the primary medicament and the needle 5. At this point, the system can be primed by dialing out a small number of units (or cocking the device 7 if only a single dose selection is possible) using a dose dial sleeve 62 (FIG. 1). Once the device 7 is primed, then activation of a needle guard 42 (see, for example, FIG. 3) of the medicated module 4 may allow dispense of the medicaments by subcutaneously injecting the medicaments via activation of a dose button 11 on the device 7. The dose button 11 can be any triggering mechanism that causes the dose of the primary medicament that was set by the dose dial sleeve 62 to move towards the distal end 32 of the device 7. In a preferred embodiment, the dose button 11 is operably connected to a spindle (not explicitly shown) that engages a piston in the primary reservoir of the primary medicament. In a further embodiment, the spindle is a rotatable piston rod comprising two distinct threads.

One embodiment of the medicated module 4 is illustrated in FIGS. 2 and 7. In these embodiments, the medicated module 4 contains a capsule 31 comprising a reservoir 22, two keepers 20a and 20b, and two seals 6a and 6b. Reservoir 22 contains a fixed single dose of a secondary medicament. In some cases this secondary medicament may be a mixture of two or more drug agents that can be equal to or different from the primary drug compound in the drug delivery device 7. Preferably, the capsule 31 is permanently fixed within the medicated module 4, however, in some cases it may be preferred to design the module 4 such that the capsule 31 can be removed when empty and replaced with a new capsule.

In the embodiments shown in FIGS. 5 and 7, capsule 31 has ends that are sealed with pierceable membranes or septa 6a and 6b that provide a hermetically sealed and sterile reservoir 22 for the secondary medicament. A primary or proximal engagement needle 5 can be fixed in a upper or proximal hub 51 connected to the proximal end of housing 10 of the module 4 and configured to engage capsule 31 when needle guard 42 is moving in the proximal direction during injection. The outlet or distal needle 3 is preferably mounted in a lower hub 53 and initially protrudes into lower keeper 20b. The proximal end of needle 3 may pierce the lower septum 6b when the coupling member 52 rotates and is moved proximally by the force exerted by needle guard 42 and a biasing member or spring 48 during injection.

When first attached to the delivery device 7, the medicated module 4 is set at a pre-use or starting state. Preferably, an indicator 41 shows through a window 54 to inform the user of the pre-use condition of the medicated module 4. The indicator 41 is preferably a color stripe or band provided on the outer surface of the proximal end of guard 42 (see FIG. 3) and visible through an aperture (window 54) in the outer body. The needle guard 42 is slidably engaged with the inner surface of outer housing 10 by engagement of arms 2 provided on the outer surface of the needle guard 42 and channels 1 provided on the inner surface of the housing 10 (see FIGS. 4 and 6). Retention snaps 56 (see FIG. 6) may prevent the guard 42 from disengaging the outer housing 10 at its fully extended position. Housing 10 partially defines an internal cavity 21 that holds coupling member 52 (FIG. 4), which contains capsule 31. A portion of the proximal end of housing 10 defines the upper hub 51 that holds needle 5. Optionally, as illustrated in FIG. 7, a shoulder cap 25 may be added to the proximal outer surface of outer housing 10. This shoulder cap 25 can be configured to serve as indicia to identify to a user the type/strength of secondary medicament contained in the module 4. The indicia can be tactile, textual, color, taste or smell indicia.

FIG. 7 shows a cutaway or cross-sectioned view of the medicated module 4 set in the pre-use or starting state, where needles 3 and 5 are not piercing septa 6a and 6b. In this position, the coupling member 52 is at its most extended position and needles 3 and 5 are not in fluid communication with the secondary medicament contained in capsule 31. The capsule 31 is supported by the coupling member 52. In this neutral or suspended state of capsule 31, primary medicament from the cartridge in cartridge holder 50 of device 7 can flow through needle 5 into keeper 20a, through bypass 46 and into keeper 20b, and eventually out through needle 3. This flow configuration may allow the user to perform a priming step or procedure by setting a small dose of the primary medicament using the dose dial sleeve 62 and dose button on the drug delivery device 7.

The compression spring 48 (see FIG. 3) is positioned between the distal end of coupling member 52 and the inner proximal face of guard 42 to bias the guard 42 into an extended (guarded) or distal position as illustrated in FIG. 7. Upon assembly, spring 48 is purposely compressed to supply a proximally directed biasing force against lower hub 53. This pre-compression of spring 48 is possible because the lower hub 53 and the coupling member 52 are prevented from moving in an axial proximal direction by a radial stand off 40 (see FIG. 6) located on the inner surface of the outer housing 10 that engages with an upper stand off pocket 66 (see FIG. 3) and legs 17 of lower hub 53 that engage with lower stand off pocket 65. The combination of these stand-offs/legs and pockets prevent the lower hub and upper hub needle 3 from piercing into the centre of the capsule 31 until the device 7 is triggered as previously described.

Figure 3:
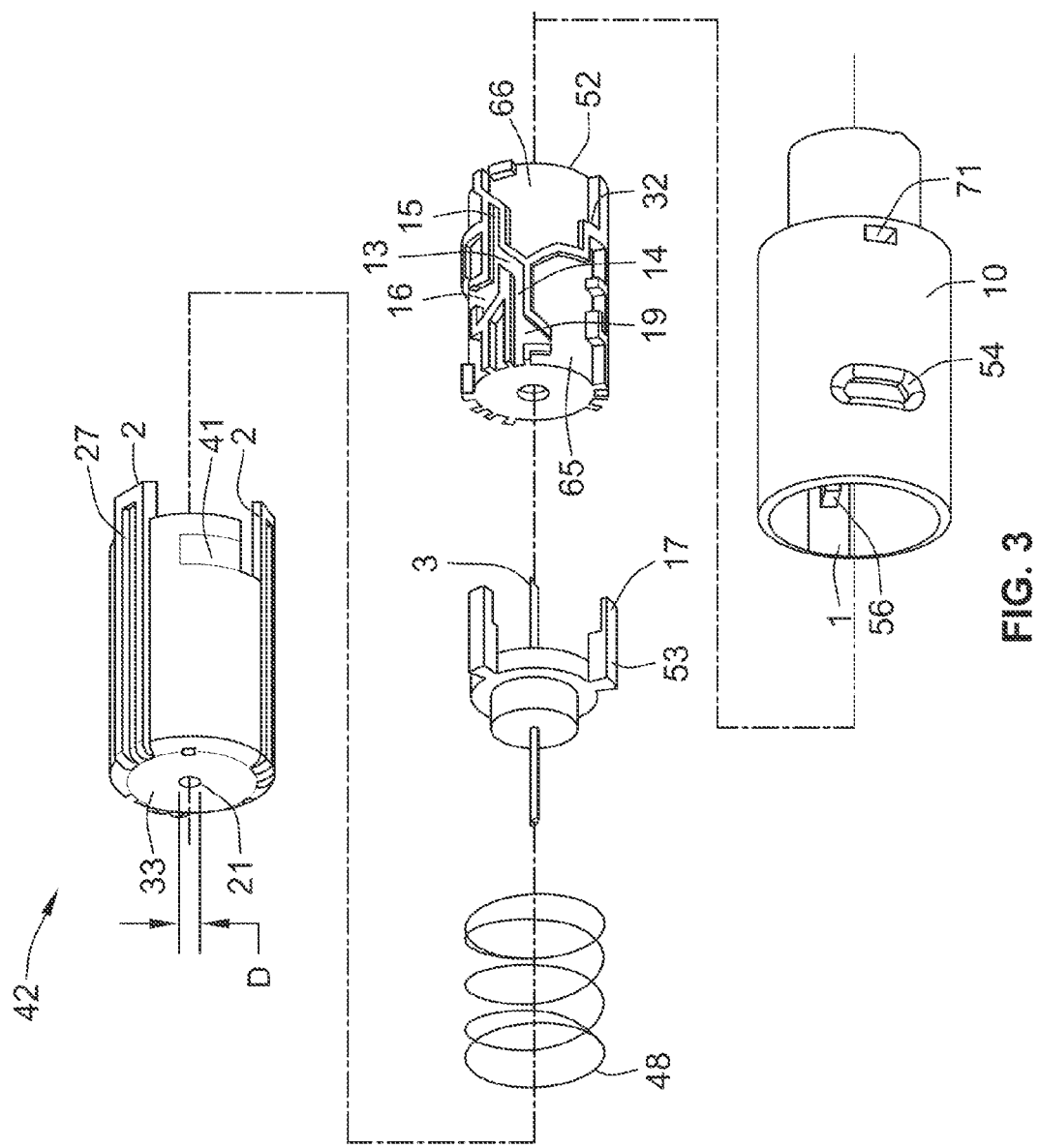
FIG. 3 illustrates an exploded distal perspective view of all the components (except the medicated capsule) of the medicated module illustrated in FIG. 2.

The proximal inner surface of guard 42 has one or more inwardly protruding features, drive teeth, pips, or like structures 12 that run in one or more tracks 13 or guide ways formed in the outer surface of coupling member 52. As shown in FIG. 3, track 13 can be described as four paths, 19, 14, 15, and 16, that have a specific geometry such that after a single use of the medicated module 4 the drive tooth 12 may be blocked from further axial movement and the guard 42 (and, hence, the device 7) is "locked" in a guarded position, where the distal end of the needle 3 is completely and safely covered by the needle guard 42.

One unique feature of the medicated module assembly is the user feedback that is given when the assembly is used. In particular, the assembly could emit an audible and/or tactile "click" to indicate to the user that he has, firstly, triggered the device 7 and, secondly, reached the "commit" point such that the needle guard 42 will lock safely out upon completion of the injection/removal of the guard 42 from the injection site. This audible and/or tactile feature could work as follows. As mentioned, the needle guard 42 is rotationally constrained by outer housing 10 and has one or more drive teeth 12 that are initially in path 19 of track 13 on coupling member 52. As the needle guard 42 is moved proximally, the spring 48 is further compressed exerting additional force in the proximal direction on lower hub 53, which is initially constrained axially by the lower stand off pocket 65 engaged with legs 17. Likewise, the coupling member 52 is constrained from moving proximally by an upper stand off pocket stop 132 of upper stand off pocket 66 engaged with stand off 40 on the inner surface of outer hosing 10. The drive teeth 12 travel in path 19 causing the coupling member 52 to rotate slightly. This rotation will disengage the upper stand off 40 from upper standoff pocket stop 132 allowing the drive teeth 12 to enter path 14, and unblocks legs 17 from lower standoff pocket 65 allowing the coupling member 52 to move proximally carrying with it capsule 31, where it then can engage needles 3 and 5. As the needle guard 46 continues to move proximally, the drive teeth 12 move from path 14 past transition point 14*a* into path 15 causing further rotation of the coupling member 52. As this rotation is completed, the drive teeth 12 transition to path 13, potentially emitting an audile "click" sound, as well as a tactile feel, to the user. This transition past point 15*a* (and the corresponding point directly below it on the track 13) constitute the "commit" point and as such, once it has been reached the needle guard 42 will "lock out" when it extends distally upon removal of the device 7 from the injection site.

As mentioned, the distal end of the needle guard 42 has a planar surface 33 that provides an added measure of safety and reduces the pressure exerted by the needle guard 42 on the injection site during an injection with the needle assembly. Because the planar surface 33 substantially covers access to needle 3, the user is prevented from gaining access to the distal tip of the needle 3 as soon as the assembly, in particular the needle guard 42, is in the locked position. Preferably, the diameter D of needle pass through hole or internal cavity 21 in the planar surface is no more than 10 times that of the outer diameter of needle cannula 3.

The outer proximal surface of the needle guard 42 preferably has the indicia 41 that are preferably at least two different color stripes or bands, each of which is sequentially visible through the opening or window 54 in outer housing 10. One color could designate the pre-use or prime state of the module 4 and the other color would indicate that the module 4 is in finished or locked state, another color could be used to denote the transition through the trigger or "commit" point 15*a* in case a user stops injection after trigger point but before "commit" point 16*a*. For example, a green color could be the pre-use position and a band of red color could be used to indicate that the module 4 has been used and is locked and an orange color could indicate that the device 7 has been triggered but not locked out. Alternatively, graphics, symbols or text could be used in place of color to provide this visual information/feedback. Alternatively, these colors could be displayed using the rotation of the bypass cavity and printed on or embedded into the coupling member 52. They could be visible through the aperture 54 by ensuring that he needle guard 42 is made form a transparent material.

Figure 8:
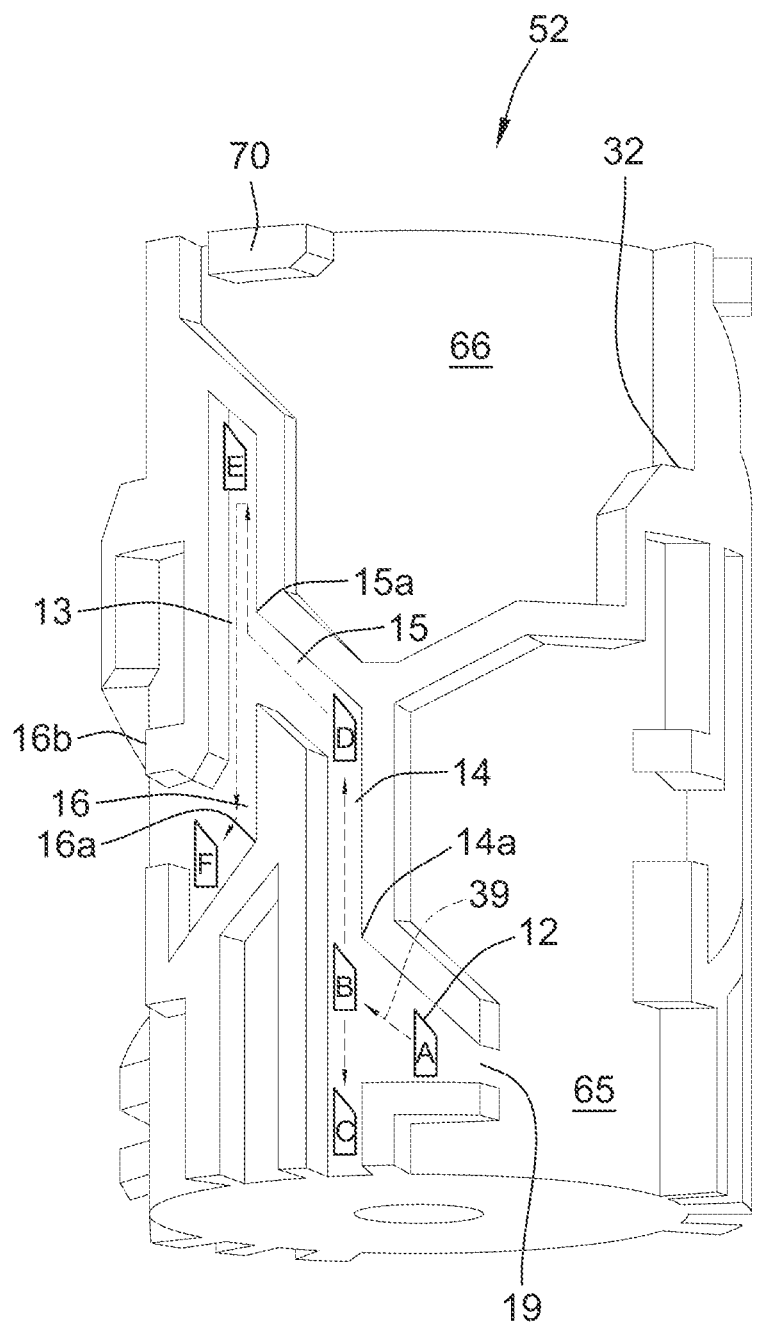
FIG. 8 is a close-up perspective view of the coupling member of the embodiment of the medicated module shown in FIG. 2 to illustrate the positions of the drive tooth of the needle guard during use.

FIG. 8 illustrates the travel of drive teeth 12 in one or more tracks 13 as illustrated by directional arrow 39. Drive tooth 12 begins at position A and through axial movement of the needle guard 42 biases the coupling member 52 rotationally until it moves past the transition point 14*a* and arrives at position B. Once the drive tooth 12 reaches position B the coupling member 52 and lower needle hub 53 move proximally causing the capsule 31 to engage needles 3 and 5, and the drive tooth 12 moves relatively to position C (this is termed as the triggering of the device 7) and it is the coupling member 52/lower hub 53 moving proximally under the release of stored energy that results in the effective position of the needle guard drive tooth 12 being position C. It is important to note that the needle guard 42 does not move under the action of the release stored energy, it is just the needle hub 53 and the coupling member 52 that move relatively away from the needle guard 42 at the point of triggering, hence the drive tooth 12 moves from position B to position C. As the needle guard 42 continues to retract, drive tooth 12 moves proximally in path 14 to position D, where it exerts a rotational bias on the coupling member 52 causing it to rotate again until tooth 12 passes the transition 15*a* (commit point) into path 16. The drive tooth 12 then moves proximally until position E is reached. At this point, the needle guard 42 is fully retracted and the full available insertable length of the needle 3 is exposed. Once the user removes the needle guard 42 from contact with the skin, the needle guard 42 begins to extend as a result of the distal biasing force exerted by spring 48 on the inner proximal surface of the needle guard 42. The utilization of the stored energy spring 48 to act both as a trigger/piercing spring and also, once extended post triggering, as the needle guard spring 48 is a unique aspect of this design. It negates the need to use two separate springs for these separate functions by locating the spring 48 in a position such that it can fulfill both roles. Initially, for example during assembly or manufacture of the medicated module 4, the biasing member 48 is compressed exerting a force on the lower hub 53/coupling member 52 in preparation for triggering. Once triggered, it extends proximally where upon it can then be compressed from the distal end as the needle guard 42 retracts against it. This secondary compression provides the force to push the needle guard 42 back to the extended and locked position as it is removed from the injection site. As the needle guard 42 moves to its fully extended post-use position, which preferably is less extended than the starting position, the drive tooth 12 moves distally in path 15 until it reaches transition point 16a, where it then rotationally biases the coupling member 52 to rotate yet again until tooth 12 enters path 16 and arrives at position F. This last rotation of coupling member 52 causes a lock out boss 70 provided on the coupling member 52 to engage a lock out feature 71 provided on the outer housing 10. This prevents any further rotational or axial movement of the coupling member 52. The needle guard 42 is prevented from further substantial axial movement, as defined earlier, by engagement of the drive tooth 12 with an axial stop 16b. It is within the scope of the invention that a number of tooth arrangements and/or profiles could be used to fulfill the required function described above, e.g., simple equal tooth profiles or more complex multi-angled profiles. The particular profile being dependent upon the required point of commit and rotation of the coupling member 52. It is also within the scope of the invention that a similar axial/rotational locking of the lower needle hub 53 to the coupling member 52 as of the coupling member 52 to the outer housing 10, could be integrated to prevent movement of the needle 3 post-triggering and post-lock out.

In any of the above described embodiments, the secondary medicament may be either in a powdered solid state, any fluid state contained within the secondary reservoir 22 or capsule 31, or coated to the inside surface of the drug dispense interface. The greater concentration of the solid form of the medicament has the benefit of occupying a smaller volume than the liquid having lower concentration. This in turn reduces the ullage of the medicated module 4. An additional benefit is that the solid form of the secondary medicament is potentially more straightforward to seal in the secondary reservoir than a liquid form of the medicament. The device 7 would be used in the same manner as the preferred embodiment with the secondary medicament being dissolved by the primary medicament during dispense.

Figures 9, 10:
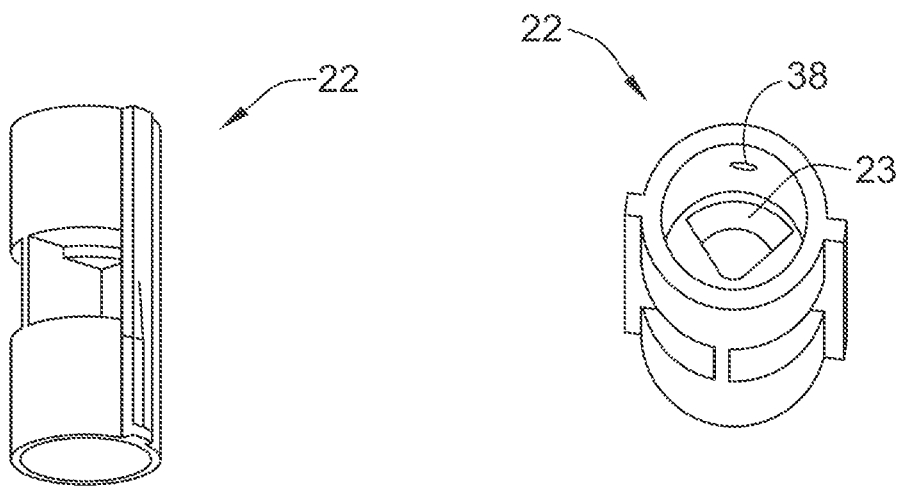
FIG. 9 is a perspective view of the reservoir of the medicated module of FIG. 2.
FIG. 10 is another perspective view of the reservoir of the medicated module of FIG. 2.

To minimize diffusion of the secondary medicament contained in the capsule 31 within the medicated module 4 into the primary medicament during dispense of the medicaments the reservoir 22 has an integral flow distributor 23. This flow distributor 23 also ensures efficient expulsion of the secondary medicament from the system and greatly minimizes residual volume. One possible embodiment of the reservoir 22 and flow distributor 23 is illustrated in FIGS. 9 and 10. Preferably the reservoir 22 and flow distributor 23 are manufactured as a single part from materials that are compatible with the secondary medicament, most preferably as a single molded piece. A preferred material would be that typically used to manufacture septa or pistons (bungs) found in multi-dose medicament cartridges, although any material that is compatible with the medicament during long term storage would be equally applicable. The flow distributor 23 is configured and positioned in reservoir 22 such that the secondary medicament fills flow channels that are defined by the shape and location of one or more channels (not shown) inside the reservoir 22. The shape of the flow channels can be optimized for a plug flow of medicament by varying the dimensions of the flow distributor 23 and/or channels. The cross-sectional area of the annulus formed between the flow distributor 23 and the wall of the reservoir 22 should be kept relatively small. The volume available to store the secondary medicament would equal the internal volume of the reservoir 22 minus the volume of the flow distributor 23. Therefore, if the volume of the flow distributor 23 is marginally smaller than the internal volume of the capsule 31, a small volume is left which the secondary medicament occupies. Hence, the scale of both the capsule 31 and the flow distributor 23 can be large while storing a small volume of medicament. Resultantly for small volumes of secondary medicament (e.g. 50 micro liters), the reservoir 22 can be of an acceptable size for handling, transport, manufacture, filling and assembly.

Preferably, the medicated module 4 is provided by a drug manufacturer as a stand-alone and separate device that is sealed to preserve sterility. The sterile seal of the module 4 is preferably designed to be opened automatically, e.g. by cutting, tearing or peeling, when the medicated module 4 is advanced or attached to the drug delivery device 7 by the user. Features such as angled surfaces on the end of the injection device 7 or features inside the module 4 may assist this opening of the seal.

The medicated module 4 should be designed to operate in conjunction with a multiple use injection device 7, preferably a pen-type multi-dose injection device, similar to is the device illustrated in FIG. 1. The injection device could be a reusable or disposable device. By disposable device it is meant an injection device that is obtained from the manufacturer preloaded with medicament and cannot be reloaded with new medicament after the initial medicament is exhausted. The device may be a fixed dose or a settable dose and, preferably, a multi-dose device; however, in some cases it may be beneficial to use a single dose, disposable device.

A typical injection device contains the cartridge or other reservoir of primary medication. This cartridge is typically cylindrical in shape and is usually manufactured in glass. The cartridge is sealed at one end with a rubber bung and at the other end by a rubber septum. The injection device is designed to deliver multiple injections. The delivery mechanism is typically powered by a manual action of the user, however, the injection mechanism may also be powered by other means such as a spring, compressed gas or electrical energy. In a preferred embodiment, the delivery mechanism comprises a spindle that engages the rubber bung or piston in the reservoir. In a further embodiment, the spindle is a rotatable piston rod comprising two distinct threads.

Exemplary embodiments of the present invention have been described. Those skilled in the art will understand, however, that changes and modifications may be made to these embodiments without departing from the true scope and spirit of the present invention, which is defined by the claims.

REFERENCE NUMERALS 1 channels
2 engagement arms
3 distal needle
4 medicated module
5 proximal needle
6a top septum/membrane/seal
6b bottom septum/membrane/seal
7 drug delivery device
8 attachment means/connector 9 connection means/attachment means
10 housing
12 drive tooth
13 track
14 path
14a transition point
15 path
15a transition point
16 path
16a transition point
16b axial stop
17 legs
19 path
20a, 20b keepers
21 hole/internal cavity
22 reservoir
23 flow distributor
25 shoulder cap
31 capsule
32 distal end of device
33 planar surface
39 path/directional arrow
40 radial stand off
41 indicia
42 guard
46 bypass
48 spring/biasing member
50 cartridge holder
51 upper hub
52 coupling member
53 lower hub
54 window
56 retention snap
62 dose setter/dose dial sleeve
65 lower stand off pocket
66 upper stand off pocket
70 lock out boss
71 lock out feature
132 upper stand off pocket stop

The invention claimed is:

1. A medicated module attachable to a drug delivery device comprising:
   an outer housing comprising a proximal needle cannula,
   a needle guard configured to provide protection of a distal needle cannula,
   a coupling member adapted and arranged to mechanically cooperate with the needle guard, at least one track being provided on an outer surface of the coupling member, wherein the at least one track comprises a first path and a second path, and
   a reservoir provided within the coupling member, the reservoir comprising a single dose of a medicament,
   wherein the needle guard comprises at least one drive tooth provided on an inner surface of the needle guard, the at least one drive tooth being configured to mechanically cooperate with the first and second paths of the at least one track.

2. The medicated module of claim 1, wherein each of the at least one drive tooth is configured to mechanically cooperate with one respective track of the at least one track.

3. The medicated module of claim 1, wherein the further comprising a lower hub configured to be engaged with the coupling member and to be engaged with the needle guard.

4. The medicated module according to claim 1, wherein the needle guard is axially moveable with respect to the housing between an extended and a retracted position, and wherein the medicated module comprises a biasing member configured to bias the needle guard towards the extended position.

5. The medicated module according to claim 4, wherein the biasing member is configured to be engaged between an internal proximal face of the needle guard and a lower hub, and wherein the biasing member is adapted and arranged to exert a force onto the lower hub when the needle guard is pushed in the proximal direction causing the lower hub and the coupling member to move in the proximal direction, thus causing the reservoir to come into fluid communication with the proximal needle cannula and the distal needle cannula.

6. The medicated module according to claim 1, wherein the at least one track further comprises third and fourth paths.

7. The medicated module of claim 6, wherein the at least one drive tooth is configured to mechanically cooperate with the first, second, and third paths of the at least one track during retraction and partial extension of the needle guard and further to mechanically cooperate with the fourth path during final extension of the needle guard into a locking position where the needle guard is fully extended in a post-use position, wherein in the post-use position, the needle guard is configured to be prevented from further axial movement with respect to the housing.

8. The medicated module according to claim 7, wherein the medicated module comprises a bypass configured to allow a dose of a primary medicament contained in the drug delivery device to bypass the reservoir when the needle guard is in the pre-use position before fluid communication is established between the reservoir and the proximal needle cannula and the distal needle cannula.

9. The medicated module according to claim 8, wherein the bypass is arranged on an inner surface of the coupling member.

10. The medicated module according to claim 6, wherein the coupling member further comprises a lower stand off pocket configured to mechanically cooperate with legs provided on a lower hub for preventing movement of the coupling member and the lower hub in the proximal direction with respect to the outer housing when the at least one drive tooth mechanically cooperates with the first path of the at least one track as the needle guard moves proximally.

11. The medicated module according to claim 10, wherein movement of the at least one drive tooth from the first path into the second path is configured to disengage an upper stand off pocket from a radial stand off such that proximal movement of the coupling member and the lower hub is allowed for establishing fluid communication of the reservoir and the proximal needle cannula and the distal needle cannula.

12. The medicated module according to claim 6, wherein the needle guard is rotationally constrained by the housing, the coupling member is rotationally constrained when the at least one drive tooth mechanically cooperates with the second or third paths of the track, and wherein the medicated module is configured to provide an audible and/or tactile indication to a user when the coupling member rotates as the at least one drive tooth moves from the second path to the third path as the needle guard moves proximally.

13. The medicated module according to claim 1, wherein the reservoir comprises a single molded component having an internal cavity with an integral flow distributor which is configured to guide flow of a fluid within the reservoir to help expelling the medicament from the reservoir.

14. The medicated module according to claim 1, wherein the housing comprises one or more openings configured for viewing indicia provided on an outer surface of the needle guard or of the coupling member, wherein the indicia are configured to indicate one or more of a pre-use position, a triggered state, where the reservoir is in fluid communication with the proximal needle cannula, or a locked position where the needle guard is in a post-use position.

15. The medicated module according to claim 1, wherein the medicament in the reservoir comprises a GLP-1 or a premix of insulin and a GLP-1.

16. A drug delivery system configured to deliver two or more medicaments operable through a single dispense interface, comprising, a primary reservoir of medicament containing at least one primary medicament; a single dispense interface configured for fluid communication with the primary reservoir; and the medicated module according to claim 1.

17. The drug delivery system of claim 16, wherein the at least one primary medicament is configured to flow via the bypass and through the single dispense interface when the needle guard is in a pre-use position.

18. The drug delivery system of claim 16, wherein mechanical cooperation of the needle guard with a second path of the at least one track of the coupling member is configured to enable the medicament in the reservoir of the medicated module to be dispensed along with the at least one primary medicament through the single dispense interface.

19. The drug delivery system according to claim 16, comprising a dose button operably connected to the primary reservoir of medicament, wherein activation of the dose button causes the at least one primary medicament to be dispensed through the single dispense interface.

20. The medicated module according to claim 1, comprising
a lower hub configured to hold the distal needle cannula,
wherein the coupling member comprises an upper stand off pocket configured to mechanically cooperate with a radial stand off provided on the housing, and
wherein movement of the coupling member and the lower hub in the proximal direction with respect to the outer housing is prevented when the upper stand off pocket and the radial stand off are engaged.

* * * * *